United States Patent [19]
Aittamaa et al.

[11] Patent Number: 5,637,777
[45] Date of Patent: Jun. 10, 1997

[54] PROCESS AND APPARATUS FOR PREPARING TERTIARY ALKYL ETHER

[75] Inventors: Juhani Aittamaa, Helsinki; Isto Eilos, Porvoo; Juha Jakkula, Kerava; Petri Lindqvist, Porvoo, all of Finland

[73] Assignee: Neste OY, Espoo, Finland

[21] Appl. No.: 302,837

[22] PCT Filed: Mar. 18, 1993

[86] PCT No.: PCT/FI93/00097

§ 371 Date: Sep. 16, 1994

§ 102(e) Date: Sep. 16, 1994

[87] PCT Pub. No.: WO93/19031

PCT Pub. Date: Sep. 30, 1993

[30] Foreign Application Priority Data

Mar. 18, 1992 [FI] Finland ............... 921173

[51] Int. Cl.$^6$ ............... C07C 41/42; C07C 43/00
[52] U.S. Cl. ............... 568/697; 203/DIG. 6; 203/DIG. 16; 203/DIG. 19; 203/29; 203/34; 203/94; 203/98; 203/99
[58] Field of Search ............... 568/697; 202/159, 202/160, 161, 162; 203/DIG. 6, DIG. 16, DIG. 19, 29, 34, 94, 99, 98; 422/187, 188, 191, 193, 195, 198, 234, 235

[56] References Cited

U.S. PATENT DOCUMENTS

| | | |
|---|---|---|
| 3,629,478 | 12/1971 | Haunschild . |
| 4,503,265 | 3/1985 | Schleppinghoff et al. ............ 568/697 |
| 5,130,102 | 7/1992 | Jones, Jr. ............ 422/191 |
| 5,177,283 | 1/1993 | Ward ............ 585/446 |
| 5,235,102 | 8/1993 | Palmer et al. ............ 562/607 |

*Primary Examiner*—Gary Geist
*Assistant Examiner*—Rosalynd A. Williams
*Attorney, Agent, or Firm*—Birch, Stewart, Kolasch & Birch, LLP

[57] ABSTRACT

The invention concerns a process and an apparatus for preparing tertiary ethers. According to the process, $C_4$ to $C_6$ isoolefins and possibly heavier olefins contained in the feedstock are reacted with lower aliphatic alcohols, in particular methanol or ethanol, in a catalytic distillation reactor system in order to produce the corresponding ethers. According to the invention, the reaction between the isoolefins and the alcohols is essentially carried out in at least one reactor (5–7) of the kind, which is combined with a distillation column (3) intended for product separation, by conducting at least a part of the liquid flow of the column through the reactor and returning it to a lower tray than the one from which it was taken. At least half of cation exchange resin is placed in the side reactor (5–7). In the process according to the invention, the catalyst can be rapidly changed without stopping the process. In order to improve conversion additional alcohol can be fed to at least one of the side reactors.

15 Claims, 4 Drawing Sheets

PROCESS AND APPARATUS FOR PREPARING TERTIARY ALKYL ETHER

This application is a 371 of PCT/FI93/00097, filed Mar. 18, 1993.

The present invention concerns a process in accordance with the preamble of claim 1 for preparing tertiary ethers.

According to such a process $C_4$ to $C_6$ isoolefins and possible heavier isoolefins or mixtures of said isoolefin contained in the feedstock are reacted with lower aliphatic alcohols, in particular methanol or ethanol, in a catalytic distillation reactor system in order to produce the corresponding ethers.

The invention also relates to an apparatus in accordance with the preamble of claim 15 for preparing tertiary ethers.

Catalytic (i.e. reactive) distillation is used for preparing, e.g., tert-methyl and tert-ethyl butyl ethers (in the following called MTBE and ETBE, respectively) and tert-amyl methyl ether and tert-amyl ethyl ether (in the following called TAME and TAEE, respectively). In the apparatus, the reaction takes place at the same time as the separation of the products from the feed. As far as the reaction kinetics of the system is concerned this is highly advantageous, because etherification is an equilibrium reaction in which the maximum conversion depends on the thermodynamic equilibrium of the reaction system. Thus, when MTBE is being prepared by a conventional fixed bed reactor/product separation distillation system, a isobutene conversion in the range from about 90 to about 95% is achieved, whereas reactive distillation will reach conversion rates in the range from 98 to 99%.

There are known in the art attempts to improve the conversion of the fixed bed reactor process by combining the product separation distillation with a postreactor. Thus, U.S. Pat. No. 4,503,265 (EC Erdölchemie GmbH) discloses a process for preparing MTBE, which comprises withdrawal of a side-stream from the distillation column, and circulating the side-stream via a postreactor. The MTBE yield is indicated as being in the range from 98 to 99%. In this case rather large amounts of the catalyst will have to be used in the fixed bed reactors in order to achieve the desired conversion, because the process fails to provide the same advantageous equilibrium as the catalytic distillation.

Although catalytic distillation for the time being is the most preferred way of preparing tertiary ethers, it is still hampered by some problems.

In the MTBE/ETBE/TAME/TAEE processes a catalyst comprising sulfonated poly-styrene/divinyl-benzene based cation resin is used, with particle sizes from about 0.1 to 1 mm, normally. Due to channeling of the liquid flows this kind of particles work poorly hydraulically in large industrial sized distillation columns, which increases the amount of catalyst needed. Large amounts of catalyst, however, worsen the channelling problem. Therefore, different kinds of bag/sack based processes have been developed and attempts have been made to shape the catalyst particles in the form of packings.

Another significant problem relating to catalytic distillation is the difficult replacement of the catalyst. Being arranged within the column, the catalyst is much more difficult to replace than the catalyst of a conventional fixed bed reactor. Moreover, catalyst replacement cannot be carried out as long as the unit is in operation. The prior art has often sought to reduce this problem by the use of, e.g., a prereactor which takes up the catalyst poisons.

U.S. Pat. No. 3,629,478 anticipates a catalytic distillation reactor used for separation of linear pentenes from tertiary olefines. The catalyst is placed in the downcomers of the column trays. Alternatively, instead of placing the catalyst in the downcomers, the patent suggests that the catalyst be put into small reaction vessels which would be connected to the distillation column by means of pipes. There would be one reaction vessel at each distillation tray. This alternative is not described in further detail in the specification, but it is clear that by placing the catalyst in external reactors of the suggested kind the replacement of the catalyst would be facilitated.

The use of the apparatus disclosed in U.S. Pat. No. 3,629,478 for industrial preparation of tertiary alkyl ethers, which can be used as gasoline components, is not suggested nor would it be possible either because it is not possible to place so much catalyst in the downcomers or the small vessels that the conversion level required by an industrial etherification process would be obtained.

A third significant problem related to catalytic distillation is formed by the difficulties in exactly controlling the reaction conditions. The components form different azeotropes during distillation. As far as the reaction is concerned, it is important that the alcohol/isoolefin-ratio is controlled, since a lower ratio than 1 causes dimerization/polymerization of the isoolefin in the catalyst bed, whereas, at an excess of alcohol, two alcohol molecules together form the corresponding ether.

Finally, catalytic distillation is hampered by the problem that the column has to be designed for a specific catalyst technique (sack/bag or packing), which makes it difficult in the future to change catalyst supplier.

In summary, it can be noted that the main disadvantages of catalytic distillation are:
1. poor packing hydraulics as far as mass transfer is concerned,
2. difficulties in controlling the alcohol to isoolefin ratio,
3. difficult catalyst replacement and
4. dependency on a specific catalyst supplier.

The present invention aims at eliminating the problems related to the prior art while providing an entirely novel way of preparing tertiary ethers.

The invention relies on two basic features. Firstly, the tertiary ether is prepared in a catalytic distillation reactor system, which comprises a distillation column and at least one side reaction zone. In this context, the term "side reaction zone" denotes a reaction zone to which is conducted only a part of the internal vapor-liquid-flow of the distillation column, namely the liquid flow, and even this one often partially. The gas flow instead by-passes the reaction zone. The side reaction zone can, for instance, comprise an external reactor (a side reactor) or a reaction zone placed in the distillation column, which functionally corresponds to such an external reactor. The side reaction zone contains a cationic catalyst. In the presence of that catalyst the hydrocarbons react with the alcohol and form an ether.

Secondly, in connection with the present invention it has been found that even if the mixture of hydrocarbons and alcohol which is fed into the above-described catalytic reactor system is being routed through a prereactor, for instance in order to bind catalyst poisons and improve conversion, the conversion rate of the isoolefins of the feedstock mixture remains rather low as far as the end use of the product is concerned: in case of TAME the maximum conversion typically lies in the range from about 50 to about 60% and in case of MTBE and ETBE the maximum conversion is about 70 to 80%. Therefore, according to the invention, in order to raise the conversion rate, alcohol used in the etherification reaction is fed into at least one of the side reaction zones.

In particular the process according to the invention is mainly characterized by what is stated in the characterizing part of claim 1.

The apparatus according to the invention is characterized by what is stated in the characterizing part of claim 15.

According to the first preferred embodiment of the invention the tertiary ether is prepared in a catalytic distillation reactor system, which comprises a distillation column and at least one external reactor (in the following also called the side reactor or side reactor unit). At least one side stream is taken from the distillation column, said side stream being circulated through the side reactor back to the distillation column to a tray below the one from which it was taken. The side stream conducted to the reactor comprises the total internal liquid flow of the column or a part thereof.

In contrast to the postreactor process mentioned in the introduction of the description, according to the invention, the side reactor of the distillation column is used for essentially carrying out the etherification reaction not only the after-reaction of the etherification reaction mixture, as is the case in the prior art. The side reactors used in the invention differ from the reaction vessels suggested in the U.S. Pat. No. 3,629,478 in the sense they contain so much catalyst that the conversion level required by an industrial processes is obtained. Furthermore, in connection with at least one of the reactors there is a feed nozzle for feed of additional alcohol.

According to a second preferred embodiment according to the invention the tertiary ether is prepared in a catalytic distillation reactor system, which comprises a distillation column into which a reaction zone is fitted. Said reaction zone can be operated in a similar manner as the above-described side reactor. This kind of a reaction zone is arranged in such a way that a part of the flow from above the catalyst layer flows past the layer and a part (usually the main part) through it. Having flowed through the layer, the flow is conducted to a lower tray (preferably a tray below the feed tray). In this case, the operation of the system fully corresponds to a side reactor process. The flow which by-passes the reactor represents the part of the internal liquid flow, which is not taken as a side draw in the side reactor case.

Within the scope of this invention, the expression "feed nozzle for additional alcohol arranged in connection with the side reaction zone" denotes feed means which can be used for feeding alcohol used in the etherification reaction into the reaction mixture in the reaction zone or, preferably, before said zone.

According to the invention, an "essential part" of the etherification is carried out in the side reaction zone of the distillation reactor system. For the purpose of this invention, this expression means that said at least one side reaction zone contains at least 30% of the total catalyst amount used in the etherification reaction. In one mode of operating the first preferred embodiment of the invention, the etherification reactions are carried out entirely in the side reactors. The invention can also be implemented by first routing the hydrocarbon/alcohol mixture through a prereactor, e.g., for binding the catalyst poisons, whereas a part of the catalyst is placed in the distillation column.

A catalytic reactor system consisting essentially of a distillation column and at least one side reactor unit is operated at as identical conditions of the reactive distillation as possible. The number of reactors needed depends on the isoolefin content of the reaction mixture. It also depends on whether a prereactor is used. Generally several side reactor units are used for the purpose of the invention. To the side reactors there are conducted liquid streams flowing from one tray to the other in the column. If each tray of the column is provided with a side reactor unit, conditions of the conventional reactive distillation process are reached rather closely. In this connection, it should be emphasized that the catalyst amount required by the etherification process is large and that, as a result, large side reactor units are needed for obtaining the required conversion level. The downcomers of the column or small vessel would not be able to contain enough catalyst.

According to the invention there is a minimum of one side stream and one side reactor unit and a maximum of as many side streams and side reactor units as there are trays in the distillation column for achieving the desired conversion rate or according to economical aspects. Thus, in a preferred embodiment of the invention there are 1 to 20, preferably about 2 to 3 side reactor units. The working examples described below include a one-reactor system (Example 1) as well as a multi-reactor system (Example 2).

The side reactor unit can consist of one single reactor or it can be formed of several smaller reactors which are arranged in series or parallel, or in series/parallel. Example 1 shows a reaction unit comprising three reactors arranged in series.

By placing all the catalyst needed in the catalytic reaction system in side reactors certain below-described advantages as regards, e.g., maintenance of the system are obtained.

Figure 3:
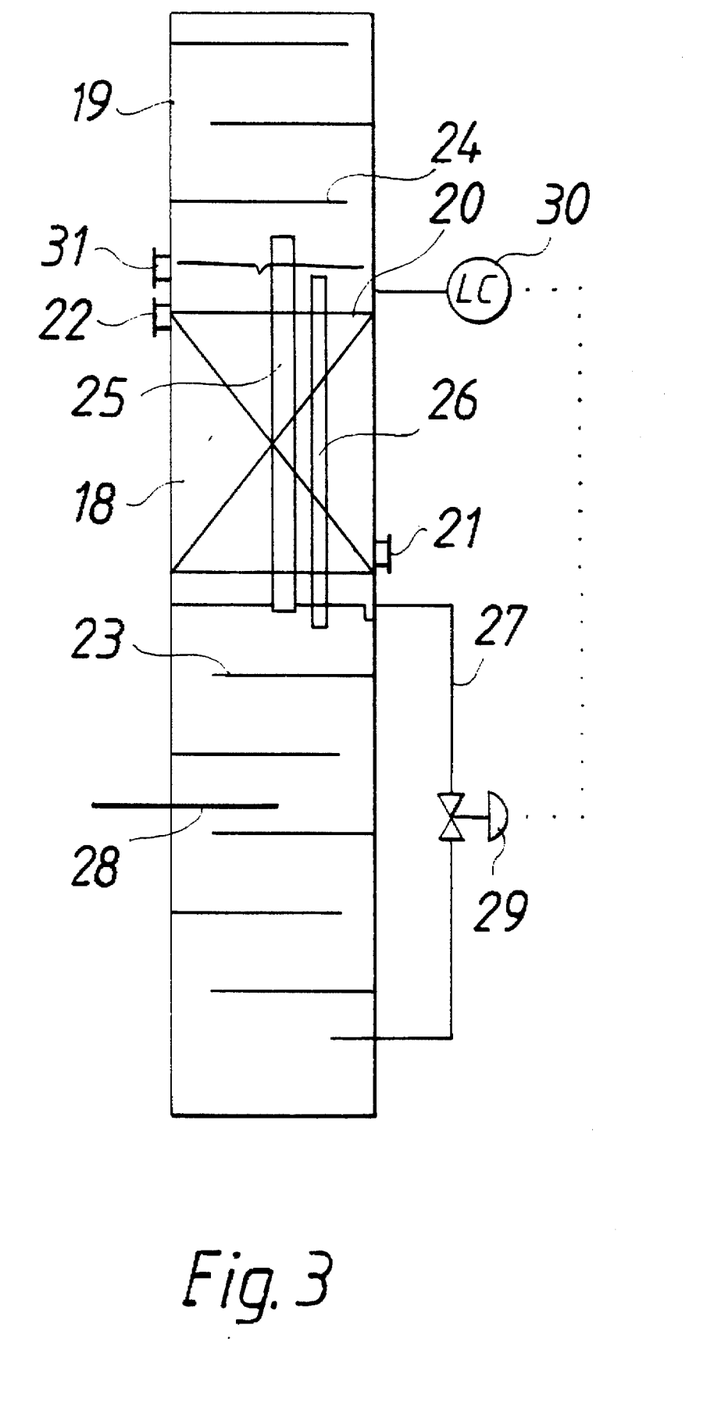
FIG. 3 shows the principal construction of a column provided with a reaction zone, the figure illustrating the novel way in accordance with the invention to place the catalyst in the column.

Within the scope of the invention the side reactor system can be implemented also by placing at least one catalyst bed inside the distillation column as known per se or in the way shown in FIG. 3.

The side draw taken from the column can be as large as the internal liquid flow of the column (total drawoff) or smaller. Total drawoff is applicable if the column is provided with several reactor units, the side stream being returned to the next tray below the drawoff tray. In the latter case, which is suitable for the one-reactor-system, the drawoff is about 40 to 90%, typically about 60 to 70% of the reflux flow, which makes it possible to circulate the flow and feed it back to the column at a suitable tray below the drawoff plate. In this case, the suitable tray is determined by the normal criteria which determine the optimum feed tray of a distillation column.

When TAME is being prepared it is advantageous to control the operation of the distillation column such that the withdrawn overhead product essentially contains only an azeotrope of $C_4$ hydrocarbons and methanol. In this case the side stream is preferably taken from a tray, which is below the trays having K-values for methanol smaller than 1. At the side draw tray the K-value may, however, be greater than 1, as Example 1 shows. The side stream is, in a similar manner, returned to the column to a trays having a K-value greater than 1. The K-value means, for the purpose of this application, the ratio $Y_i/x_i$, wherein $y_i$ represents the molar amounts of component i in the vapor and $x_i$ the molar amount of component i in the liquid. In order to control the composition of the azeotrope, the reaction mixture of the side reactor is returned to the column at a location below the feed tray of the column. As a result of this arrangement, which is described in more detail in our copending patent application, all of the unreacted methanol removed from the distillation column is bound to an azeotrope. No separate methanol washing unit is needed any longer. This means a considerable decrease of the apparatus investment costs. By means of the process described it is possible to prepare a product, which—depending on the feedstock—comprises mixtures of different ethers, said mixtures including unreacted $C_{5+}$ hydrocarbons.

The side stream circulation can be achieved as a forced circulation by pumping. Alternatively, it can be achieved by a thermosiphon, said phenomenon being caused by the reaction heat boiling the reaction media.

If the hydrocarbons are circulated by forced circulation the reactor can be a fixed bed or tubular reactor or a fluidized bed reactor or any combination of these types of reactors, or several reactors arranged in series. The advantage with forced hydrocarbon circulation is that the temperature of the side reactors and the feed back temperature can be controlled with heat exchangers. Example 4 shows how the isoamylene and isohexene conversions of the TAME process can be increased by optimization of the feed temperature of the side reactors and by partial/total evaporation of the side stream. Example 4 further indicates the surprising increase of the conversion of the $C_6$ hydrocarbons contained in the TAME process feed and of the yield of heavier ethers ($C_{7+}$), when the product of the side reactors is totally or partially evaporated before feeding into the column. This embodiment does not impair the isoamylene conversion of TAME preparation, either.

In a system operating according to the thermosiphon principle only a fixed bed or tubular reactor can be used and of these reactor types the last-mentioned is a rather poor alternative, because the vapor providing the circulation is condensated therein.

The catalyst volume of the side reactor can be in the range from 0.01 to 10 times the hourly flow rate of the liquid feed flow. Typically the volume-to-flow rate ratio is 0.1 to 1. Expressed in other terms, the LHSV of the reactor can be from 0.1 to 100 $m^3 kat/m^3 fluid/h$, typically 1–10 h.

If the reactor is a fixed bed reactor, the fluid superficial velocity in the reactor is determined according to the recommendations by the catalyst supplier, said velocity typically being 5–30 m/h for liquid flow. If the flow is directed upwards, the flow rate is determined according to the minimum fluidization rate of the catalyst. For typical ion exchange resin catalysts the minimum fluidization rate is, depending on the catalyst, 25–35 m/h when the fluid comprises a $C_5$ hydrocarbon.

If the reactor is a fluidized bed reactor the fluid superficial velocity is 1 to 10 times, typically 2 to 6 times the minimum fluidization flow rate (50–150 m/h for $C_5$ hydrocarbons).

The operating pressure of each reactor is determined by the operating pressure of the column. The pressure of the reactor is the column pressure added with the pressure losses caused by the piping, its parts, and the control valves. Therefore, the operating temperature of each reactor is determined by the boiling point of the hydrocarbon mixture. This prevents the formation of overheated zones in the reactor.

In the thermosiphon circulation a part of the liquid flowing through the side reactor is evaporated, the evaporation partially being caused by the energy released during the exothermic reaction. The evaporation can be achieved in the side reactor, in which case a preheater can be used before the side reactor, or in a boiler arranged after the reactor. The last-mentioned embodiment is preferred and for this reason the working example below describes the working principle of a process implemented according to the latter alternative. The same working principle can, however, be employed in the first-mentioned alternative, in which case the evaporation takes place in the reactor itself. The thermosiphon circulation is applicable in particular when the column/side reaction system is operated in such a way that there is a methanol consuming reaction in the system. Methanol is removed from the column only in an amount corresponding to the methanol content of the azeotrope formed by hydrocarbons and methanol. In this case the side reactor circulation is conducted to the stripping section of the column. The system operates as a kind of a side boiler.

According to the second preferred embodiment of the invention the tertiary ether is prepared in a catalytic distillation reactor system, in which there is a reaction zone placed in the distillation column, said reaction zone being functionally equivalent to the side reactor described above. As mentioned, a part of the stream coming from above the catalyst layer placed in the distillation column is conducted past the layer, and a part (normally the main part) is conducted through the layer. The vapor is at least partially conducted past the catalyst layer.

When the catalyst is placed in the column it is important, as far as the distillation and the equilibrium restrictions are concerned, that the liquid amount needed for distillation is conducted from the tray above the reaction layer to a tray below the reaction bed. It is also important that the liquid stream conducted through the reaction layer is recycled to the column to a point below the reaction layer and the feed point. By this arrangement it is possible to prevent reaction products from returning to the reaction layer.

U.S. Pat. No. 4,847,430 discusses conducting the gas through a reaction zone comprising at least two catalyst layers. There is no mention in said publication that the liquid would partially by-pass the catalyst layer nor does the publication concern the preparation of TAME. A process similar to the one disclosed in the U.S. Patent Specification is described in EP-A1 0.405.781. According to the last-mentioned process the catalyst is covered by liquid, but gas is conducted through the liquid layer. The catalyst is kept in "tea bags" in the column.

The alcohol can be fed into the side reaction zone in many ways. Thus, the side reactor can be provided with a separate alcohol feed nozzle for direct feed of the alcohol into the reactor. Similarly, a feed nozzle can be arranged in the distillation column at the site of the reaction zone according to the invention. However, the alcohol feed preferably takes place before the catalyst bed by combining an alcohol stream with the olefin/alcohol/ether mixture which is to be fed into the reaction bed. Because of this, in the side reactor case alcohol is preferably fed into the side stream taken from the distillation column before the stream is conducted to the side reactor. In particular, the alcohol is fed into the side stream before it is subjected to additional heating. The alcohol feed nozzle of the distillation column is, on the other hand, preferably fitted above the reaction zone so that the alcohol can be mixed with the condensed reaction mixture before it flows down through the reaction bed.

From the data of Example 1 it appears that by feeding additional alcohol to the side reaction zone it is possible to improve the yield of the ether; by feeding 0.5 kg/h additional methanol into the side reactor the TAME yield increases by about 15%. In addition, alcohol feed into the side reaction zone improves the controllability of the process. A vapor-liquid-equilibrium prevails during distillation. Alcohols and the reacting isoolefins are partially evaporated and leave the reaction zone which makes it difficult to control the mole ratio between the alcohol and the isoolefins. By increasing the pressure it is possible to prevent evaporation of the reacting components. This measure improves the alcohol concentration in the reaction zone. In conventional catalytic distillation the temperature of the reaction zone depends on the pressure of the column. In the side reactor the pressure and the temperature can be adjusted as desired.

According to the invention about 1 to 100% of the total amount of the alcohol is fed into the side reaction zone. It is also possible, according to the invention, to feed all the alcohol used in the etherification reaction into the side reaction zone. This procedure is applicable in particular when no prereactors are used at all. On the other hand when prereactors are used, at least the main part of the alcohol is, however, admixed with the hydrocarbon feed before the prereactors. About 1 to 50%, typically about 1 to 30% of the alcohol is then fed into the side reaction zone.

The concept according to the invention can be used for preparing all the heavy ethers mentioned in the introduction of the description. It can be used for preparing other mineral oil based ethers, as well. Pursuant to one preferred embodiment TAME or heavier ethers (for instance, tert-hexyl methyl ether, THME) are prepared. The products can be used as components of motor fuels. The feed of the catalytic distillation reactor system comprises, e.g., a hydrocarbon cut which is obtained from fluidized bed catalytic cracking and which in addition to $C_4$ and $C_5$ isoolefins also contains $C_6$ isoolefins and even heavier hydrocarbons. These components are also at least partially oxygenized in the process.

Considerable advantages are obtained by the invention in comparison to the presently commercially available reactive distillation units.

The maintenance of an apparatus provided with side reactor units is easier than that of conventional catalytic distillation units because the catalyst can be changed without opening the large distillation column. For this reason the catalyst is quickly replaced without the process having to be run down. A reserve unit made for the reactor can be taken into operation during catalyst replacement. A catalytic distillation unit working according to the invention is easily adapted to an existing old traditional process, which does not include a catalytic distillation unit.

The controllability of the reaction conditions is better in a process according to the invention than in the prior art processes. Therefore, the feed stream conducted to the reactor can be analyzed, and on basis of the analysis result alcohol or hydrocarbon feed can be increased as needed.

If the hydrocarbon recycling is effected by means of forced circulation, the whole reaction takes place controllably in the liquid phase which decreases the size of the required reaction. In contrast, in a conventional catalytic distillation unit, the diameter of the catalyst part of the column is often larger than the diameter of the column.

The invention makes it possible to optimize the temperature of the reactor, whereas in a conventional catalytic distillation unit the temperature varies according to the pressure of the column and the liquid-gas-equilibrium. The reactor pressure can be set at a higher value than the pressure of the column. It is then possible to let the reaction heat increase the temperature of the liquid without evaporation of the liquid in the reactor. Evaporation will happen in the column. Similarly, if an endothermal reaction were carried out in the apparatus, the heat can be introduced at the reactor temperature and not at the temperature of the reboiler of the column.

The invention makes it possible to use several different kinds of catalysts, and the user of the apparatus is not dependent on a specific catalyst manufacturer.

In the following the invention will be described in more detail with reference to the attached drawings.

Figure 1:
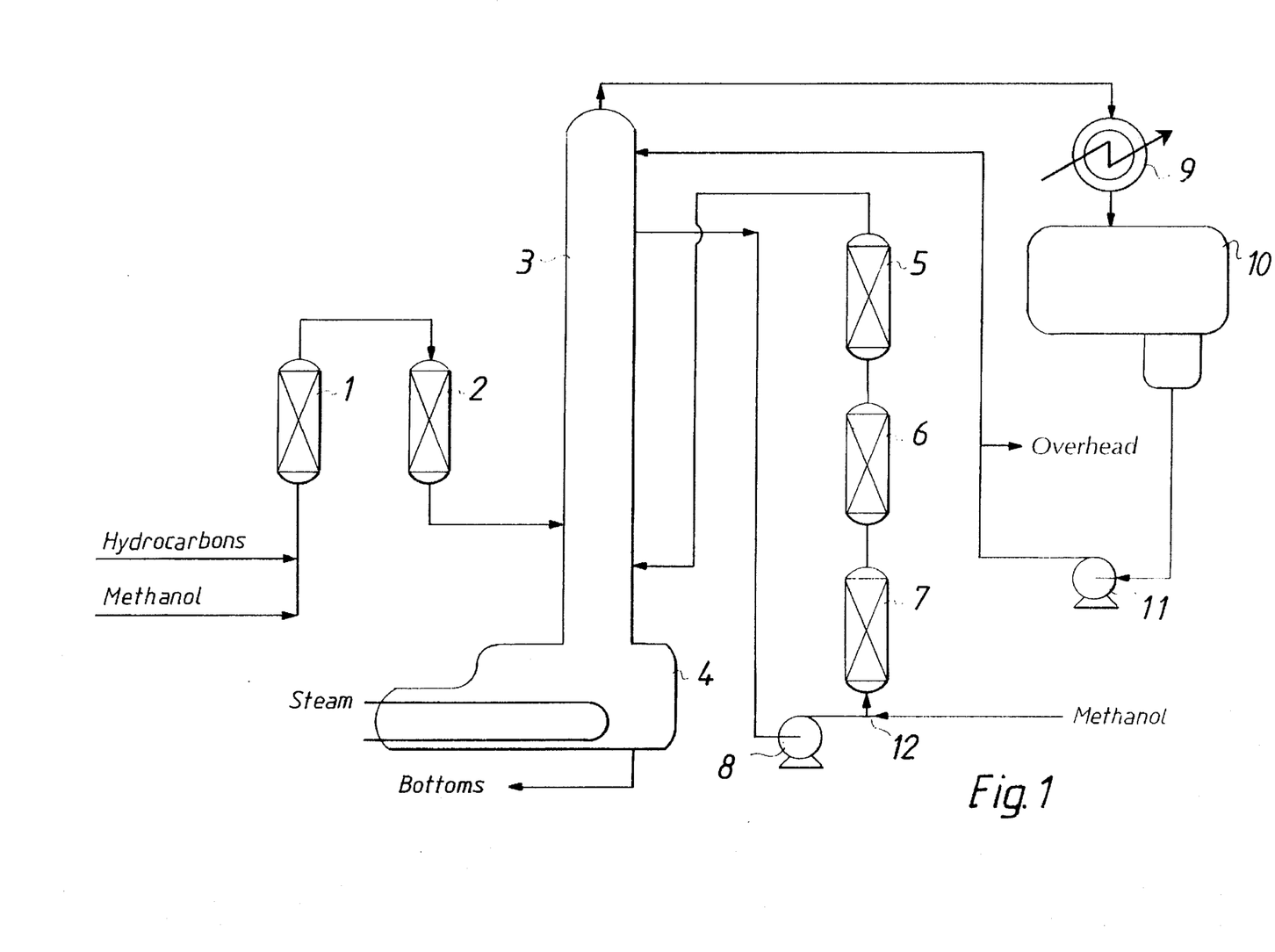
FIG. 1 depicts a simplified scheme of the TAME process described in Example 1.

In the test arrangement according to the example 1, the hydrocarbon feed and the methanol are mixed together, the mixture is heated and fed through the prereactor part 1, 2. The hydrocarbon feed may, for instance, comprise a hydrocarbon fraction containing isoolefins, such as a hydrocarbon cut of a cat cracker, containing a mixture of isoolefins. The prereactors consist of two reactors filled with ion exchange resin beds. The reactors can be fixed or fluidized bed or tubular reactors. The reactors may be arranged in series, as shown in the figure, or in parallel. If there are more than two prereactors they may also be arranged in series/parallel. Because of the reaction the temperature rise in the prereactors is about 5° to 15° C. depending on the efficiency of the reactor insulation. From the prereactors the mixture is conducted to the distillation column 3. At the bottom of the distillation column there is a steam reboiler 4. The distillation column can be of a packed column, or have valve, sieve or bubble-cap trays. The overhead of the column is removed via a condenser 9 to a reflux drum 10, from which the overhead is removed by means of a pump 11. A part of the overhead is forwarded to further processing, for instance to a MTBE process, and a part thereof is returned to the column. TAME and heavier ethers are removed with the bottoms product. In addition to the ethers, the bottoms product also contains unreacted $C_{5+}$ hydrocarbons. The reflux ratio of the column is preferably from about ½ to 200. Even greater ratios can be used in pilot plant equipments. Next to distillation column 3 a side reactor system has been arranged, which consists of three reactors 5, 6, 7 arranged in series. The reactors can, if desired, be replaced by one larger reactor. According to the mode of circulation, the reactors can be fixed bed or fluidized bed reactors or tubular reactors, as mentioned above in the general part of the description. The side reactors are fed with a liquid stream taken from the column. The pressure of the liquid stream is increased by pump 8. The side stream is preferably taken from a tray which is located below trays having methanol K-values less than 1. Additional methanol can, if needed, be fed to the side reactor feed before the side reactor. The reactor feed can be cooled to the reaction temperature before the side reactor. Due to heat losses the temperature rises only by a few degrees in the side reactors. From the side reactor system 5 to 7 the liquid flow is routed back to column 3. It is then returned to a plate having a K-value greater than 1.

Figure 2:
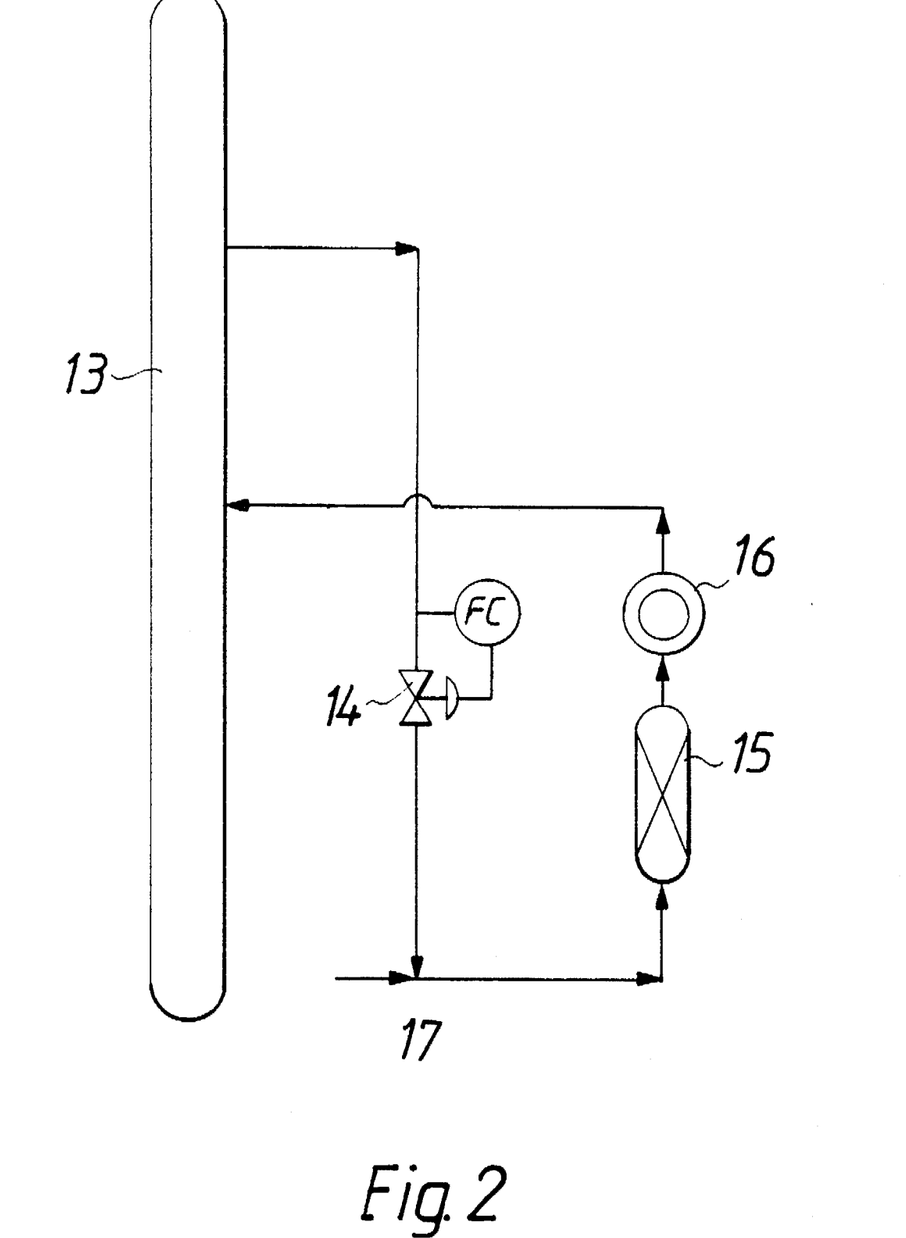
FIG. 2 shows a simplified process scheme of a thermosiphon circulation.

In the previous case, the recycling was carried out by forced circulation. FIG. 2 shows an alternative side reaction circulation, which is based on thermosiphon circulation. A side stream taken from the distillation column 13 is conducted via a flow control valve 14 to a side reactor. The side reactor is a fixed bed reactor which is filled with a cation exchange resin. The product flow is conducted to a boiler 16, which evaporates the liquid and forwards it to column 13. Alcohol can be fed into the side stream at point 17.

The thermosiphon process works as follows: if $P_1$ is the pressure of column 12 at the side drawoff tray, $P_2$ the pressure, at the surface of the liquid in boiler 16 and $P_3$ is the pressure of column 13 at the feed back tray, the pressure difference $P_2-P_3$ equals the hydrostatic pressure difference between these points added with the friction losses of the mass flow in the feed back piping between the boiler and column 13. On the other hand, $P_2-P_1$ equals the hydrostatic pressure difference between the surfaces complemented with the frictional loss caused by the mass flux in the piping leading to the boiler complemented with the pressure loss of reactor 15. Since the density of the liquid flowing to boiler 16 is considerably larger than that of the two phase flow leaving the boiler and since the elevation of the boiler 16 is higher than that of the side draw of the column, a mass flux will result so that pressure balance is achieved. In practical applications piping lengths should be minimized such that the force which drives the flow and which results from the density differences is not lost because of the frictional losses of the piping.

FIG. 3 present a way of placing the catalyst in the column is such a way that it functionally resembles a side reactor. The purpose of this embodiment is to decrease the number of equipment and control circuits needed for the TAME process. It is based on the idea methanol and the inert hydrocarbons of the etherification process are removed as an azeotrope with the distillate of the distillation. Catalytic distillation cannot be applied without methanol washing and separation because there should be exact separation between the reaction phases because of the reaction equilibrium restrictions. When, on one hand, some of the flow from above the catalyst layer by-passes the catalyst layer, and on the other, most of the flow is conducted through the layer, that flow subsequently being conducted to a location below the feed point, the operation of the system completely resembles that of a side reactor process.

There can be one of several prereactors before the column.

In the embodiment shown in FIG. 3, the catalyst bed 18 is fitted into column 19 just as it would have been placed into a fixed bed reactor. In order to prevent catalyst entrainment, a screen 20 or a similar holding means is mounted above the reaction bed. The catalyst can be removed and added, for instance, via hatches 21 and 22. Continuous removal and addition of the catalyst is also possible. Below and above the catalyst bed there are conventional distillation trays 23 and 24. The vapor flow coming from below the catalyst bed is routed through the catalyst bed (while flowing past it) via conduit 25. The liquid coming from above the catalyst bed is partially conducted via conduit 26 to the distillation tray 23 below the catalyst bed 18 in order to prevent reaction equilibrium restrictions. The conduit 26 can also be fitted inside the conduit 25 or on the outside of the column. The main part of the liquid coming from the tray above the catalyst bed flows through the catalyst bed 18 and is routed via conduit 27 to a point below the feed tray 28.

The level of the liquid above the catalyst layer is adjusted by means of a valve 29, which is controlled by a liquid surface regulator 30. The liquid head should be high enough to compensate for the pressure losses occurring in the catalyst layer 18 and between the liquid surface and the feedback point of the column 19. The liquid flow past the catalyst layer needs not necessarily be adjusted, but flow control can be implemented if the by-pass conduit is located on the outside of the column. If necessary, more alcohol can be added via the additional feed nozzle 31.

Figure 4:
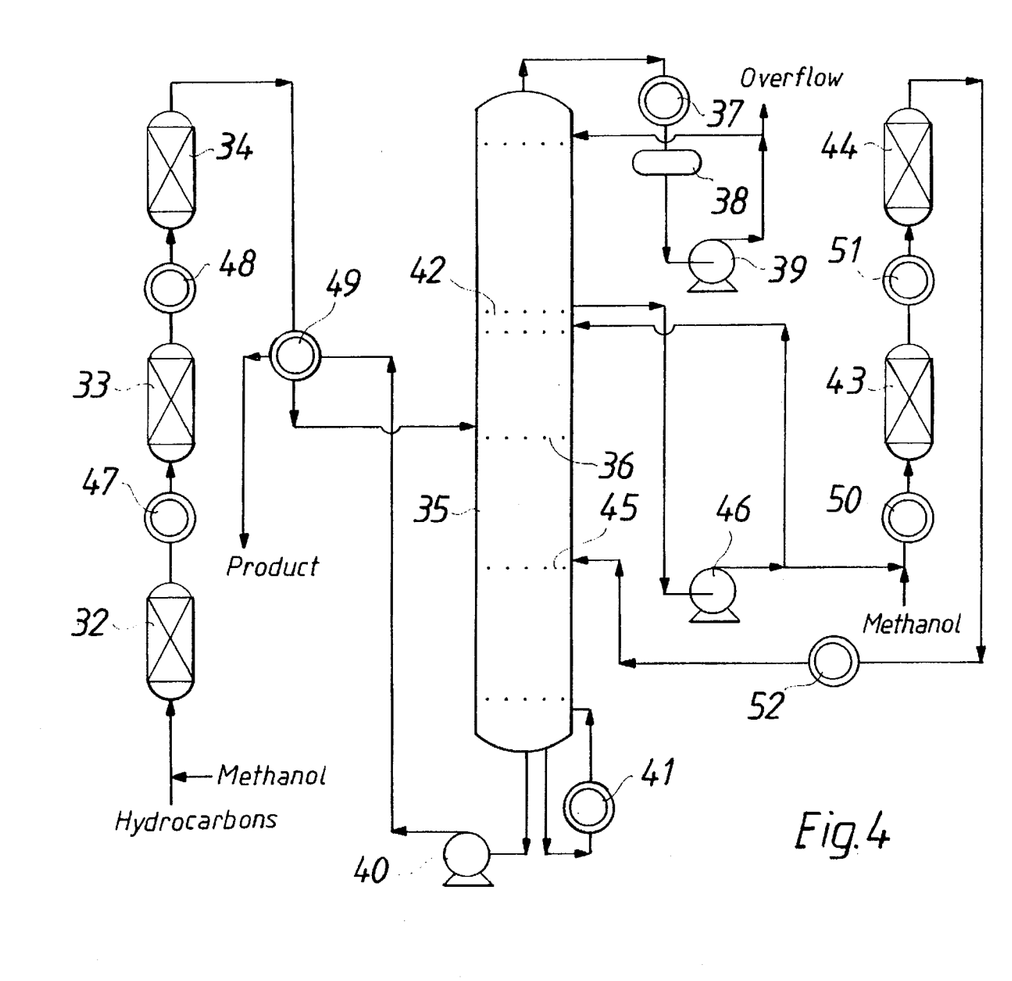
FIG. 4 depicts a simplified scheme of the TAME/TAEE process described in Example 4.

Catalytic distillation based TAME/TAEE process, with reaction stages possibly arranged before the distillation, can be carried out as described in FIG. 4.

The process embodiment according to FIG. 4 is mainly similar to the process depicted in FIG. 1. Thus, the alternative apparatus solutions are the same as in that embodiment.

The hydrocarbons and the methanol are mixed together and fed through the prereactor systems 32, 33 and 34 onto tray 36 of column 35. The column is equipped with a condenser 37 and a reflux drum 38 and a boiler 39. The bottoms product is removed with the aid of pump 40 and the condensated distillate is returned to the column with the aid of a steam reboiler 41. A part of the overhead product is removed from the process. A side stream is taken from the column (from tray 42) either as a total or as a partial draw, which is pumped through an external reactor unit 43, 44 back to the distillation column 35 to a lower tray 45 than the one from which it was taken. The circulation is a forced circulation achieved by a pump 46. Said side stream can be equal to the internal liquid flow of the column (total draw), a part of it being returned to the next tray below the drawoff tray after the pump, or the side stream can be smaller than the internal liquid flow of the column (typically 60 to 70% of the reflux flow), which makes it possible to return the stream after the reactors to a suitable tray which is located below the drawoff tray. In the latter case, the proper tray is determined by the normal criteria for deciding the optimal feed tray of the distillation column, or by measures taken for controlling the formation of an alcohol/hydrocarbon azeotrope, as described in detail in our copending patent application. As mentioned above, it is preferred for controlling the azeotrope to return the reaction mixture of the side reactor to a point below the feed tray 36 of the column.

In the embodiment shown in FIG. 4, one side circulation is used. Therefore, in order to increase the total conversion of the reaction, several side reactors 43, 44 in series are used. For the same reason, the stream introduced into each of the reactors is adjusted to an optimal temperature by heat exchangers 47–52. Since the liquid coming from the column 35 is at its boiling point and because it is desired to carry out the reaction in the liquid phase, a prerequisite for increasing the temperature is that the pressure of the reaction mixture is increased to above the pressure corresponding to the pressure of the desired boiling point. When side reactors are used; it is easiest to increase the pressure by pump 46 before the side reactors.

Methanol is fed into the reaction mixture coming from the column before this is conducted to the heat exchanger 50 of the side reactor unit 43, 44. The methanol feed point is marked with the reference numeral 53.

When TAME or TAEE are prepared, the optimal drawoff is located above the feed point of the column, whereas the feedback point is located below the feed point. The feed of the TAME and TAEE processes contains in addition to isoamylene, which will react with methanol and ethanol, respectively, and form the desired end products, also reactive $C_{6+}$ hydrocarbons, such as 2,3-dimethyl-1-butene, 2-methyl-1-pentene, 2-ethyl-1-butene, 2-methyl-2-pentene, 1-methylcyclopentene, cis-3-methyl-2-pentene, tr-3-methyl-2-pentene, 2,3-dimethyl-2-butene which react to form higher ethers (for instance tert-hexyl methyl ether). The total conversion of these compounds is limited by the fact that, being recycled to the column with the side circulation, they are partially conducted towards the bottom of the column due to unfavourable vapor-liquid equilibriums. They do not flow upwards, in which case they would be recycled to the side reactors and which would achieve a circulation of the reacting components between the feedback point and the drawoff of the side stream. Such a circulation would be advantageous as far as the total conversion of all the reacting components is concerned. The desired circulation can, however, be created by heating the stream coming from the side reactor(s) in heat exchanger 52 before it is returned to the column such that the desired components are evaporated when fed into the column and will start to flow upwards in the column. By the described arrangement, the total conversion of the process can been enhanced by very simple measures.

The following working examples elucidate the invention:

EXAMPLE 1

Preparation of TAME by Using a Catalytic Distillation Reactor System with Prereactors and Side Reactors The apparatus configuration depicted in FIG. 1 was used. The inner diameters of the prereactors 1 and 2 were 102.3 mm and their lengths were 1500 mm. They were filled with the catalyst Dowex® M-32 supplied by Dow Chemicals Inc. The catalyst comprises an acid sulfonated polystyrene/divinyl benzene based cation exchange resin. The inner diameter of the distillation column 3 was 160 mm, its height was 11,000 mm and it was provided with packings. There were 6 layers of packings. Three side reactors 5 to 7 were sequentially connected and each of them had an inner diameter of 154.1 mm, and a height of 1,150 mm. These, reactors were also filled with the catalyst Dowex® M-32.

The hydrocarbon feed rate was 30 kg/h. Its composition is shown in Table 1. The table also indicates the amount of methanol feeds. The methanol and the hydrocarbon feed were mixed together and heated to 58° C. Then the mixture was conducted through the prereactors 1 and 2, which caused the temperature to increase by 9° C. From the prereactors the mixture was conducted to the distillation column 3, the feed point being situated between the third and the fourth packed bed. The temperature of the distillation column was 40° C. at the top and 95° C. at the bottom, the operating pressure being 400 kPa. Distillate was withdrawn from the top (composition indicated in Table 1). The reflux ratio of the column was 110.

A side-stream was withdrawn from the column at a point between the second and the third packed beds. The temperature of said side-stream was 70° C. It was cooled to 60° C. and fed to the side reactors 5 to 7. The liquid feed rate was 60 kg/h. The pressure of the feed was increased by pump 8 and methanol was added, as indicated in Table 1. The temperature rose by 3° C. in the side reactors (the temperature rise depended to some extent on the heat losses). From the side reactors the flow was routed back to the column, the feedback point of the side reactor being between the fourth and the fifth packing bed.

TABLE 1

| Test results of TAME preparation | | | | | | | |
|---|---|---|---|---|---|---|---|
| Methanol feed (kg/h); | | Test 1 | | Test 2 | | Test 3 | |
| to the prereactor | | 2.4 | | 2.6 | | 2.6 | |
| to the side reactor | | 0 | | 0 | | 0.5 | |
| Component (% by weight) | Feed | Bottom | Dist. | Bottom | Dist. | Bottom | Dist. |
| $C_4$ hydrocarbons | 2.41 | 0.34 | 94.03 | 0.01 | 95.32 | 0.01 | 60.51 |
| 2-Me-1-butene | 7.50 | 0.34 | | 0.31 | | 0.13 | |
| 2-Me-2-butene | 13.74 | 6.51 | | 5.89 | | 2.51 | |
| Remaining $C_5$ | 47.91 | 45.25 | 2.56 | 44.96 | 1.91 | 44.30 | 35.08 |
| Reacting $C_6$ | 6.91 | 4.94 | | 4.89 | | 4.71 | |
| Remaining $C_{6+}$ | 21.53 | 20.36 | | 20.23 | | 20.50 | |
| Methanol | | 0.04 | 2.99 | 0 | 2.24 | 0.53 | 3.80 |
| TAME | | 20.17 | | 21.36 | | 24.51 | |
| THME | | 2.21 | | 2.21 | | 2.59 | |
| TAOH | | 0.16 | | 0.14 | | 0.20 | |
| DME | | | 0.42 | | 0.53 | | 0.61 |
| Total | 100 | 100 | 100 | 100 | 100 | 100 | 100 |
| Amount (kg/h) | 29 | 30.7 | 0.73 | 30.9 | 0.73 | 30.9 | 1.15 |

TAME = tert-amyl methyl ether
THME = tert-hexyl methyl ether
TAOH = tert-amyl alcohol
DME = dimethyl ether

TABLE 2

| K-values of the TAME column | | | | | | | | |
|---|---|---|---|---|---|---|---|---|
| | Side drawoff | | Tray above side drawoff | | Feed | | Side drawoff feedback | |
| Tray Component | Liquid wt-% | K-value | Liquid wt-% | K-value | Liquid wt-% | K-value | Liquid wt-% | K-value |
| DME | 0 | 5.3 | 0 | 4.48 | 0 | 6.76 | 0 | 6.60 |
| $C_4$ | 9.54 | 1.15 | 10.69 | 1.12 | 3.66 | 2.24 | 8.43 | 2.12 |
| MeOH | 2.24 | 1.51 | 2.34 | 0.96 | 0.18 | 4.99 | 0.12 | 4.64 |
| $C_5$ | 79.54 | 0.92 | 78.54 | 0.9 | 58.1 | 1.21 | 70.48 | 1.13 |
| 2M1B | 0.61 | 0.88 | 0.55 | 0.85 | 0.42 | 1.17 | 0.25 | 1.10 |
| 2M2B | 4.55 | 0.71 | 4.39 | 0.73 | 5.62 | 0.96 | 4.06 | 0.89 |

TABLE 2-continued

K-values of the TAME column

| Tray Component | Side drawoff Liquid wt-% | Side drawoff K-value | Tray above side drawoff Liquid wt-% | Tray above side drawoff K-value | Feed Liquid wt-% | Feed K-value | Side drawoff feedback Liquid wt-% | Side drawoff feedback K-value |
|---|---|---|---|---|---|---|---|---|
| TAME | 0 | 0.19 | 0 | 0.17 | 4.15 | 0.33 | 3.66 | 0.30 |
| TAOH | 0.05 | 0.23 | 0 | 0.21 | 0.09 | 0.88 | 0.10 | 0.82 |
| 2M2P | 0.04 | 0.31 | 0 | 0.31 | 4.76 | 0.45 | 2.54 | 0.41 |
| THME | 0 | 0.07 | 0 | 0.06 | 1.05 | 0.14 | 0.67 | 0.13 |

2M1B = 2-methyl-1-butene
2M2B = 2-methyl-2-butene
2M2P = 2-methyl-2-pentene

EXAMPLE 2

System Comprising Several Side Reactors— Preparation of ETBE

The test apparatus employed was otherwise similar to the one described in example 1, but the prereactors 1 and 2 were not used and the two intermediate packing layers of the distillation column were substituted by a side reactor system. There were 8 side reactors. A total liquid drawoff was taken to each of the side reactors and the reaction product was recycled to a tray below the drawoff tray. Each side reactor had a catalyst volume of 2.7 liters. The column operated in pilot plant scale and the distance between the liquid drawoff tray and the feedback tray was large enough to ensure that there was a free liquid flow circulation through the side reactor. On an industrial scale, forced circulation can be used.

The hydrocarbon feed was introduced into the column below the lowest feedback tray of the side reactor and the ethanol was fed above the drawoff to the uppermost sidereactor. The results are indicated in Table 3.

TABLE 3

Results of the ETBE run

| Hydrocarbon feed: | | Ethanol feed: | |
|---|---|---|---|
| Isobutene | 22.33 p-% | Ethanol | 99.38 p-% |
| Isobutane | 31.58 | ETBE | 0.16 |
| n-butane | 10.03 | $H_2O$ | 0.46 |
| 1-butene | 12.82 | | |
| Trans-2-butene | 12.94 | | |
| Cis-2-butene | 9.27 | | |
| $C_{5+}$ | 1.03 | | |
| Amount | 33 kg/h | Amount | 5.2 kg/h |
| Column effluent: | | Bottoms product of the column: | |
| Isobutene | 6.90 p-% | Ethanol | 0 p-% |
| Isobutane | 37.50 | ETBE | 95.06 |
| n-butane | 11.82 | $H_2O$ | 0 |
| 1-butene | 15.20 | TBA | 0.70 |
| Trans-2-butene | 15.19 | $C_{5+}$ | 2.49 |
| Cis-2-butene | 10.75 | $C_{4-}$ | 1.75 |
| $C_{5+}$ | 0 | | |
| Ethanol | 2.64 | | |
| Amount | 27.8 kg/h | Amount | 10.4 kg/h |

The operational pressure of the column was 0.75 MPa. The temperature at the top of the column was 49° C., at the bottom 146° C. and in the side reactors 60° to 70° C. Ethanol was fed to the uppermost side reactor.

EXAMPLE 3

Thermosiphon Circulation

The side stream circulation through a side reactor described in Example 1 can also be achieved by means of a thermosiphon, as explained above in connection with FIG. 2. In the working example the following conditions were used:

Elevation of the drawoff of the stream which is conducted from column 13 to side reactor 15: 7500 mm
Elevation of side reactor 15: 1000 mm
Elevation of boiler 16: 2500 mm
Elevation of feed back point: 3500 mm The pressure of the column 13 was 405 kPa at the drawoff and 410 kPa at the feed back point. The length of the conduit between the column and the side reactor 15 was 11 m and its diameter was 9 m. The length of the conduit connecting the reactor 15 with the heat exchanger 16 was 1 m and its diameter was 9 mm. The length of the piping from the heat exchanger 16 to the column 13 was 3 m.

The total flow of the circulation was 60 kg/h, 30% of which was evaporated in the heat exchanger. The density of the liquid was 575 kg/m$^3$ and that of the vapor 10.7 kg/m$^3$.

Pressure balance of the system:

| | |
|---|---|
| Pressure at drawoff | +405 kPa |
| Liquid hydrostatic pressure (ρgh) | +28 kPa |
| Pressure loss in piping (liquid) | −3 kPa |
| Flow measurement | −5 kPa |
| Control valve | −8.7 kPa |
| Reactor | −0.4 kPa |
| Heat exchanger | −4.5 kPa |
| Hydrostatic pressure (2-phase flow) | −0.3 kPa |
| Pressure loss in piping (2-phase flow) | −1.1 kPa |
| Column pressure at feed back | +410 kPa |

EXAMPLE 4

Increase of the Overall Conversion of the Reactive Components of an Etherification Reaction Carried Out in a Reactive Distillation Unit by Intermediate Cooling and Preheating of the Feed Back Stream TAME was prepared by the process configuration shown in FIG. 4. The column used was a packed column and the reactors had fixed beds.

Description of the test apparatus:

| | |
|---|---|
| Prereactors (32–34): | Inner diameter 102.3 mm, length 1500 mm. Filled with catalyst DOWEX M-32 |
| Distillation column (35): | Inner diameter 160 mm, hight 11,000 mm, provided with packings. The number of packing layers: 6. |
| Side reactors (43, 44): | Inner diameter 154.1 mm, hight 1150 mm. Filled with catalyst DOWEX M-32 |
| Hydrocarbon feed point: | Interspace between 3rd and 4th packing layer |
| Side draw: | Interspace between 2nd and 3rd packing layer |
| Feedback point of the side stream: | Interspace between the the 4th and 5th packing layer |
| Test conditions: | Column pressure 400 kPa Temperature at side draw: 70° C. Side stream cooled to 58° C. before feeding into first side reactor. Methanol added to side stream before feeding into first sidereactor. |

Hydrocarbon feed 30 kg/h, the composition of which is presented in Table 4, and the methanol feed (amount shown in Table 4) are mixed together and heated to 67° C. Then the mixture was routed through prereactors 32–34. After each prereactor there is a heat exchanger 47–49, whose temperature is adjusted according to Table 4. The temperature raises in the prereactors by 5°–15° C. depending on the efficiency of the heat insulation. The mixture from the prereactors is introduced into the distillation column 35.

The temperature at the top of the distillation column is 40° C. and the temperature of the bottom is 95° C., the operational pressure being 400 kPa. Distillate is drawn off from the top of the column (composition shown in Table 4). Reflux ratio in the column: 100.

The amount of the liquid feed of the side reactors 43, 44 is 49 kg/h. Feed pressure is raised by pump 46, then methanol is added to the feed (Table 4) and it is cooled to 67° C. The temperature increases in side reactor 43 by 3° C. (depends to some extent on the heat losses). From the side reactor the stream is routed via the heat exchanger to side reactor 44 (feed temperature 44° C.), and then it is recycle to the column via heat exchanger 52, which is use for heating the stream to 105° C.

TABLE 4

Compositions, temperatures and pressures of the streams (wt.-%)

| | Stream | | | | | | | | | |
|---|---|---|---|---|---|---|---|---|---|---|
| Component | 1 | 2 | 3 | 4 | 5 | 6 | 7 | 8 | 9 | 10 |
| $C_4$ | 2.09 | 0 | 1.95 | 85.58 | 2.32 | 0 | 2.32 | 2.31 | 2.31 | 0.15 |
| 2-Me-1-Bu | 1.82 | 0 | 0.38 | 0.03 | 0.34 | 0 | 0.34 | 0.24 | 0.13 | 0.07 |
| 2-Me-2-Bu | 11.67 | 0 | 4.83 | 0.06 | 4.04 | 0 | 4.04 | 1.94 | 1.69 | 1.32 |
| Rest Of $C_5$ | 31.34 | 0 | 29.21 | 9.59 | 55.78 | 0 | 55.78 | 55.64 | 55.64 | 29.51 |
| 2-Me-1-Pe | 2.23 | 0 | 1.18 | 0 | 0.62 | 0 | 0.62 | 0.34 | 0.30 | 0.70 |
| 2-Me-2-Pe | 9.52 | 0 | 6.27 | 0 | 2.80 | 0 | 2.80 | 2.12 | 1.98 | 5.14 |
| Rest Of $C_{6+}$ | 41.33 | 0 | 38.56 | 0 | 14.13 | 0 | 14.13 | 14.09 | 14.09 | 37.21 |
| Methanol | 0 | 99.95 | 2.10 | 4.68 | 17.89 | 99.95 | 17.89 | 16.75 | 16.52 | 83 ppm |
| TAME | 0 | 0 | 10.67 | 0 | 2.08 | 0 | 2.08 | 5.24 | 5.77 | 16.53 |
| THME | 0 | 0 | 4.83 | 0 | 0 | 0 | 0 | 1.32 | 1.57 | 7.31 |
| TAOH | 0 | 0 | 0.02 | 0 | 0 | 0 | 0 | 0.01 | 0.01 | 2.06 |
| DME | 0 | 0 | 0 | 0.06 | 0 | 0 | 0 | 0 | 0 | 0 |
| Water | 0 | 0.05 | 0 | 0 | 0 | 0.05 | 0 | 0 | 0 | 0 |
| Total | 100 | 100 | 100 | 100 | 100 | 100 | 100 | 100 | 100 | 100 |
| Amount (kg/h) | 30 | 2.41 | 32.41 | 0.58 | 48.75 | 0.13 | 48.75 | 48.75 | 48.75 | 31.83 |
| Temperature (°C.) | 63 | 20 | 75 | 40 | 72 | 20 | 67 | 44 | 103 | 104 |
| Pressure (bar) | 8 | 8 | 5 | 4 | 4 | 8 | 8 | 8 | 8 | 4 |

Streams:
1 Hydrocarbon feed to side reactors 32–34
2 Methanol feed to side reactors 32–34
3 Stream from prereactors to column 35
4 Column 35 effluent
5 Side drawoff flow to side reactors 43, 44
6 Methanol feed 53 to side reactors
7 Side reactor 43 feed
8 Side reactor 44 feed
9 Recycled flow immediately before entering the column 35
10 Bottoms product

TABLE 5

| Conversion rates/% | After the side reactors | Overall |
| --- | --- | --- |
| 2-Methyl-1-butene | 91 | 98.4 |
| 2-Methyl-2-butene | 39.1 | 83.5 |
| 2-Methyl-1-pentane | 72.5 | 83.8 |
| 2-Methyl-2-pentene | 14.2 | 30.9 |

We claim:

1. A process for preparing alkyl ethers, which comprises reacting isoolefins or mixtures thereof with at least one lower aliphatic alcohol in the presence of a catalyst comprising an acid cation exchange resin in order to form tert-alkyl ethers, carrying out the reaction between the isoolefins and the alcohols essentially in at least one side reaction zone, which is connected to a distillation column intended for product separation, by conducting at least a portion of the liquid flow of the distillation column through the reaction zone and returning it to a lower tray than the one from which it was taken in said distillation column, and feeding alcohol used in the etherification reaction to at least one of the side reaction zones.

2. The process according to claim 1, wherein $C_4$ to $C_6$ isoolefins and possibly heavier isoolefins are subjected to the reaction.

3. The process according to claim 1, further comprising feeding 1 to 100% of the alcohol used for etherification to the side reaction zone.

4. The process according to claim 1, further comprising forming a reaction mixture of the isoolefins and the alcohol, the reaction mixture being fed through at least one prereactor to the distillation column, and feeding 1 to 30% of the alcohol used for etherification to the side reaction zone.

5. The process according to claim 1, wherein the tertiary ether is prepared in a catalytic distillation reactor system, which comprises said distillation column and at least one external side reactor.

6. The process according to claim 5, wherein a total drawoff is taken from a drawoff tray to the side reactor, and the reaction product of the side reactor is returned to the next tray below the drawoff tray.

7. The process according to claim 5, wherein a partial drawoff is taken from a drawoff tray to the side reactor, and the reaction product of the side reactor is returned to a return tray, below the drawoff tray, the return tray being selected such that the best total conversion is obtained.

8. The process according to claim 1, wherein a liquid stream is fed to the side reaction zone from a tray above a feed tray of the distillation column, and the reaction mixture obtained from the side reaction zone is conducted to a tray below the feed tray.

9. The process according to claim 5, wherein 1 to 20, side reactors are connected to the distillation column.

10. The process according to claim 5, further comprising adjusting the temperature and pressure of the side reactor and the recirculation temperature of the side stream with heat exchangers in order to increase the ether yield.

11. The process according to claim 5, characterized by vaporizing the side reactor product at least partially before recirculating it to the column in order to increase the yield of heavier ethers.

12. The process according to claim 1, which further comprises preparing the tertiary ether in a catalytic distillation reaction system, wherein a reaction zone comprising a catalyst layer is placed within the distillation column, by-passing the catalyst layer with gas flow coming from underneath the reaction zone, and routing a first portion of liquid flow coming from above the reaction zone past the catalyst layer and a second portion through it, the second portion of liquid which flows through the catalyst layer being further routed to below a feed tray of the distillation column.

13. The process according to claim 1, further comprising recycling a side stream taken from the distillation column to below a feed tray of the distillation column for the olefins and the alcohol.

14. The process according to claim 1, further comprising circulating a side stream taken from the distillation column by the thermosiphon principle through the side reactor and back to the distillation column.

15. The process according to claim 5, wherein 2 to 3 side reactors are connected to the distillation column.

* * * * *